United States Patent [19]

Kishi et al.

[11] Patent Number: 4,972,827
[45] Date of Patent: Nov. 27, 1990

[54] GUIDE DEVICE FOR PERCUTANEOUS INSERTION OF ENDOSCOPE

[75] Inventors: Yukitoshi Kishi; Kenji Abe, both of Omiya, Japan

[73] Assignee: Fuji Photo Optical Co., Ltd., Omiya, Japan

[21] Appl. No.: 470,136

[22] Filed: Jan. 25, 1990

[30] Foreign Application Priority Data

Feb. 6, 1989 [JP] Japan .................................. 1-25735
Dec. 28, 1989 [JP] Japan ................................. 1-338467

[51] Int. Cl.⁵ .............................................. A61B 1/00
[52] U.S. Cl. ....................................................... 128/3
[58] Field of Search ................................ 128/3, 4, 6, 7

[56] References Cited

U.S. PATENT DOCUMENTS

| 2,256,942 | 9/1941 | Duffy | 128/3 |
| 3,132,645 | 5/1964 | Gasper | 128/3 |
| 4,332,242 | 6/1982 | Chikama | 128/3 |
| 4,712,536 | 12/1987 | Hawks | 128/3 |

*Primary Examiner*—William H. Grieb
*Attorney, Agent, or Firm*—Oblon, Spivak, McClelland, Maier & Neustadt

[57] ABSTRACT

Described herein is a guide device for an endoscope to be percutaneously introduced into a body, the guide device including a trocar having an obturator extractably inserted in an outer sheath, and a guide tube to be placed in the outer sheath in place of the obturator of the trocar. The guide tube is rounded off at the inner edge of its fore end which is to be protruded from a sharp-edged tip end of the outer sheath when placed therein.

7 Claims, 5 Drawing Sheets

GUIDE DEVICE FOR PERCUTANEOUS INSERTION OF ENDOSCOPE

BACKGROUND OF THE INVENTION

1. Field of the Invention

This invention relates to a guide device for securing a path of insertion of a percutaneous type endoscope like a laparoscope or a thorcoascope to be percutaneously introduced into a body.

2. Description of the Prior Art

In terms of the path of insertion, the endoscopes which are used for examination or for diagnostic or therapeutic purposes are classified into a direct type which is inserted into a body directly through an oral or nasal cavity and a percutaneous type which is inserted through the skin of a body. In case of a percutaneous type endoscope, it is necessary to secure a path of insertion beforehand by the use of a guide device. In this regard, it has been the general practice to resort to the so-called trocar.

The trocar is usually composed of an obturator and an outer sheath. The obturator which is placed in the outer sheath in a coupled state is extracted as soon as the fore end of the trocar pierced through the skin reaches an intracorporeal cavity portion which needs an examination or a remedial treatment, thereby securing a path of insertion for the insert body of an endoscope to be introduced to the cavitary portion. For the purpose of facilitating the percutaneous penetration, the tip end of the obturator is formed in a sharp-pointed conical shape, while the tip end of the outer sheath is likewise formed in a sharp-edged shape in the fashion of a blade edge.

In order to ensure safe percutaneous penetration with the trocar and at the same time to permit smooth intracavitary observation or remedial treatment, the cavitary portion is filled with an insufflation gas. For this purpose, the trocar is provided with a valve means for opening and closing a passage in the outer sheath. This valve is arranged to close the passage automatically upon extraction of the obturator from the outer sheath and can be opened with a finger or fingers when introducing the insert portion of the endoscope. Since the valve is open state while thrusting the insert portion into the outer sheath, the dimensional difference between the inner diameter of the outer sheath and the outer diameter of the insert portion is made minimal to prevent leaks of the insufflation gas through the gap between the inner and outer peripheral surfaces of the outer sheath and the insert portion of the endoscope.

The percutaneous type endoscopes which have been adopted as laparoscopes and thoracoscopes are mostly rigid endoscopes each having a rigid insert body which consists of a hard member like a metal tube. Recently coming into use are angle type endoscopes which have an angle portion provided between a hard or rigid insert body and a hard tip member for the purpose of turning an observation window or a therapeutic instrument outlet in the tip member into a desired direction. Also coming into use are endoscopes which have a flexible portion between an angle portion and a rigid insert body which is connected to a manipulating portion of the endoscope.

As well known in the art, the angle portion usually has a ring structure which consists of a plural number of flexibly connected ring units and which is covered under a protective net with an outer skin layer of soft material such as rubber, polyurethane or the like. Similarly to the angle portion, the flexible portion is covered with an outer skin layer of soft material such as rubber, polyurethane or the like.

In case of an endoscope with such an angle portion, however, its insert portion which is protruded from the outer sheath of the trocar is likely to be damaged by the sharp-edged tip end of the sheath when extracted from the outer sheath after angling the fore end of the insert body for intracavitary diagnosis or examination or a therapeutic treatment. Particularly, since the outer surface of the angle portion more or less contains undulations, it is more likely that the edge portion of the outer sheath will bite on and scrape off the outer skin layer of the angle portion. Further, in a case where a flexible portion is provided contiguously to an angle portion, the outer skin layer on the flexible portion, which is protruded from the sheath, could be scraped off when its fore end portion is bent together with the angle portion. Above all, in a case where the dimensional difference between the outer diameter of the insert portion and the inner diameter of the sheath is minimized in order to reduce leaks of the pneumoperitoneum gas, it is very probable that the outer skin layer on the insert portion be damaged as a result of contact with the sharp-edged tip end of the outer sheath at the time of extraction of the endoscope if the angle portion or a contiguous portion is curved state even in a slight degree.

The scratching bruises or partial scraping-off of the outer skin layer not only impairs the appearance of the layer but also makes it extremely difficult to clean and disinfect the damaged portions. Besides, there are possibilities that scraped fragments of the outer skin layer might remain in the body. Such a dangerous situation has to be precluded in as a secure manner as possible.

SUMMARY OF THE INVENTION

In view of the foregoing situations, it is an object of the present invention to provide a guide device for percutaneous type endoscope with an angle portion, which can guide the insert body of the endoscope smoothly into and out of an outer sheath without damaging the outer skin layer on the angle portion or on an portion contiguous to the angle portion.

It is another object of the invention to provide a guide device for percutaneous type endoscope, which can guide the insert body of the endoscope smoothly into and out of an outer sheath in place of an obturator of a trocar, securely maintaining an intracorporeal cavity in hermetically sealed state as long as the insert body is placed in.

In accordance with the present invention, the above-stated objects are achieved by the provision of a guide device for a percutaneous type endoscope with an angle portion at the tip end of an insert body thereof, the guide device essentially including: a trocar having an outer sheath, and an obturator extractably inserted in the outer sheath; and a guide tube to be inserted into the outer sheath in place of the obturator to form a path of insertion for the insert body of the endoscope, and having a tip end formed in a non-edged shape and protrudable over a predetermined length from the tip end of the outer sheath when inserted therein.

BRIEF DESCRIPTION OF THE DRAWINGS

In the accompanying drawings:

FIGS. 1 through 5 illustrate a first embodiment of the present invention, of which:

FIG. 1 is a schematic view of an endoscope as a whole;

FIG. 2 is a sectional view of a trocar;

FIG. 3 is a sectional view of a guide tube;

FIG. 4 is a sectional view of a tip end portion of the guide tube; and

FIG. 5 is a partly cutaway elevation of the endoscope and the guide device in coupled state.

DESCRIPTION OF PREFERRED EMBODIMENTS

Figure 1:
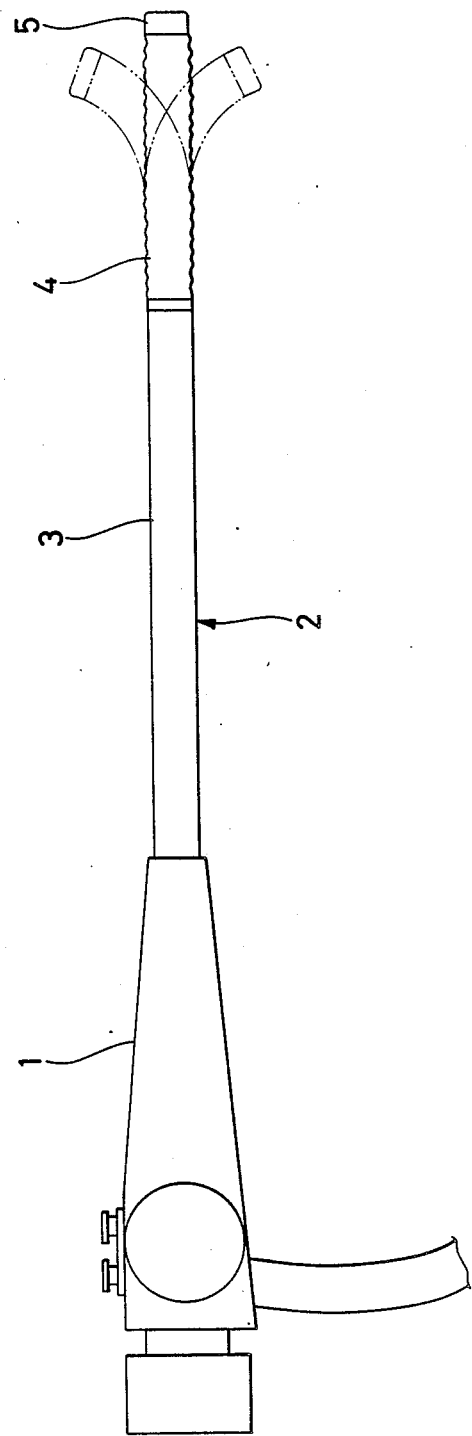

Now, the invention is described more particularly by way of the preferred embodiments shown in the drawings.

Referring first to FIG. 1, there is shown the general construction of an endoscope according to the invention, in which indicated at 1 is a manipulating portion, and at 2 is an insert body of the endoscope. The insert portion 2 is provided with a hard or rigid portion 3 which is formed of a pipe of metal or other rigid material and which is extended contiguously from the manipulating portion over a predetermined length. Extended contiguously from the fore end of the hard portion 3 is an angle portion 4 which is provided with a hard tip portion 5 with an instrument outlet for protruding therethrough an illumination window, an observation window or a therapeutic instrument such as forceps. The angle portion 4 serves to turn the hard tip portion 5 into a desired direction, and, as well known in the art, has a triple-layer construction having a protective net and an outer skin layer successively fitted on a ring structure consisting of a number of pivotally connected ring units. The outermost skin layer is formed of a soft material like rubber or polyurethane.

Figure 2:
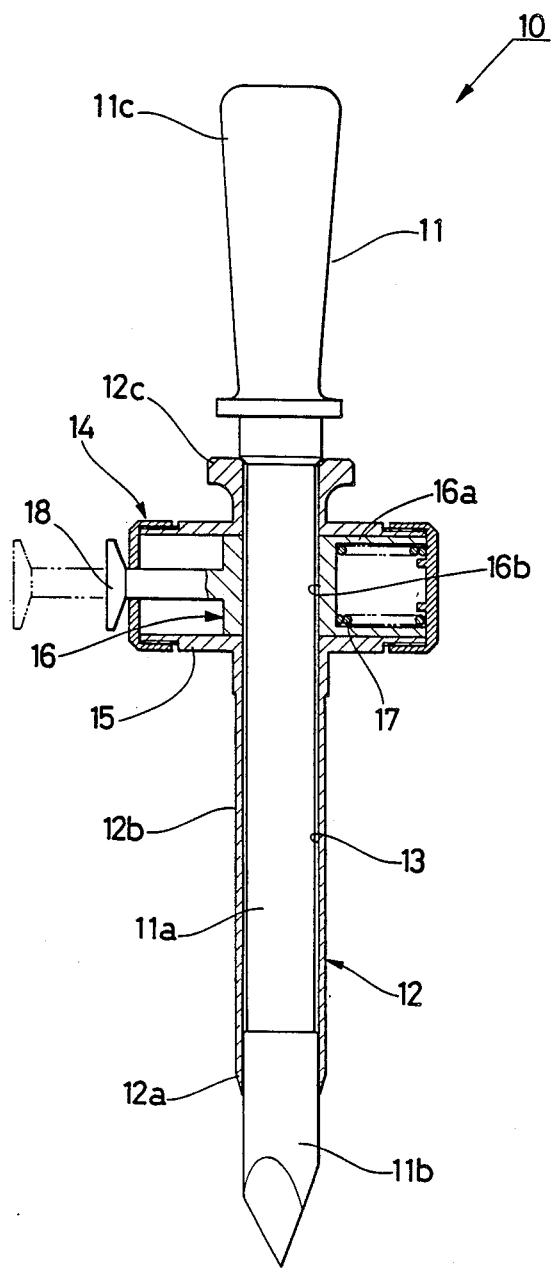

Shown in FIG. 2 is the general construction of a trocar 10 which serves as a guide for the insert body 2 of the endoscope, wherein indicated at 11 is an obturator and at 12 is an outer sheath of the trocar. Contiguously forward of a rigid portion 11a, the obturator 11 is provided with a tip end 11b which is formed in a sharp-pointed conical shape suitable for percutaneous penetration. The base end 11c to be gripped by an operator of the obturator 11 is formed in a knob-like shape.

On the other hand, the outer sheath 12 is constituted by a tubular member of metal or other suitable material, which tubular member having a passage 13 for receiving therein the obturator 11 or the insert body 2 of the endoscope and a fore end portion 12a with a blade-like sharp edge. In order to avoid formation of a stepped surface at the bladed end of the outer sheath 12, the fore end portion of the obturator 11 is formed in a slightly larger diameter than other portions thereof. Provided on the cylindrical body portion 12b of the outer sheath 12 is a valve member 14 for opening and closing the passage 13, the valve member 14 including a cylindrical valve casing 15 connected to the outer sheath 12 perpendicularly across the passage 13, and a valve body 16 slidably fitted in the valve casing 15. The valve body 16 has a blocking portion 16a for closing the passage 13, and a communicating opening 16b of the same diameter as the passage 13. The valve body 16 is constantly urged by a spring 17 to assume a blocking position where the blocking portion 16a is located across the passage 13 to hold same in closed state. The valve body 16 is provided with a pusher 18 at the end remote from the blocking portion 16a, and moved against the action of the spring 17 when the pusher is pressed in with a finger, whereupon the opening 16b is shifted into a position in alignment with the passage 13 to switch the latter into open state.

Figure 3:
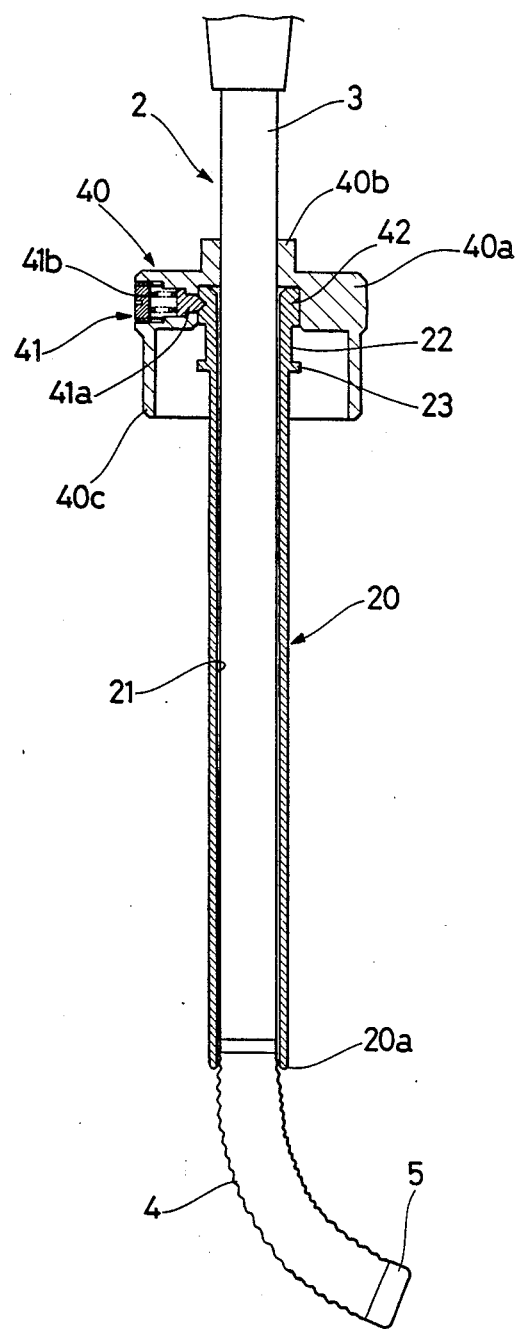
Figure 4:
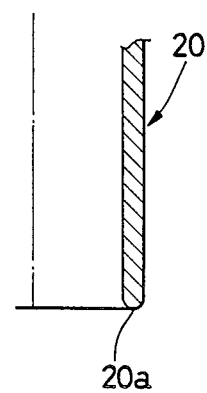

In this instance, the insert body 2 of the endoscope is placed in the passage 13 of the outer sheath 12 of the trocar 10 not directly but through a guide tube 20. As shown particularly in FIG. 3, the guide tube 20 is formed of a rigid pipe of metal or other suitable material having an outer diameter slightly smaller than the inside diameter of the outer sheath 12 and internally defining a passage 21 for receiving the insert body 2 of the endoscope. The guide tube 20 terminates in a fore end portion 20a free of sharp edges, namely, in a fore end portion 20a with edges rounded off arcuately as shown in section in FIG. 4. The guide tube 20 is longer than the outer sheath 12 in axial length, and, when inserted in the outer sheath 12 in coupled state, its fore end portion 20a protrudes from the tip end 12a of the outer sheath 12 by a predetermined length l.

To lock the guide tube 20 within the outer sheath in the coupled state, a hook 30 is pivotally mounted on the bulged base end 12c of the outer sheath 12. The hook 30 is pivotable about an axis 31 and constantly urged by a spring 32 in the direction of insertion of the guide tube 20. On the other hand, the guide tube 20 is provided with an extension 22 at its base end, the extension 22 serving as a stopper for delimiting the depth of insertion of the guide tube 20 into the outer sheath 12 and provided with a locking flange for engagement with the hook 30.

Figure 5:
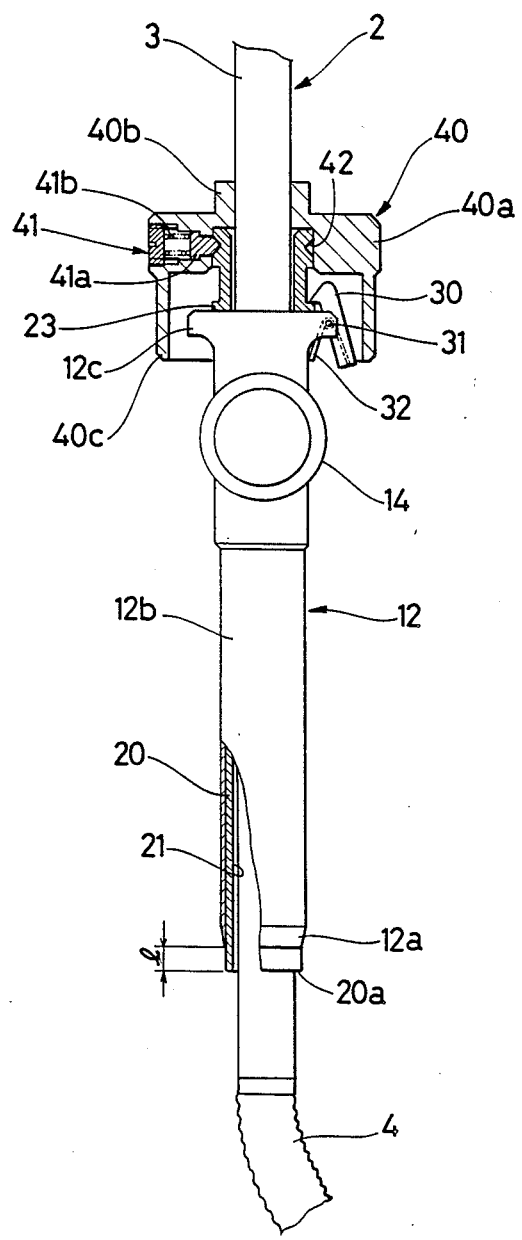

Denoted at 40 is a hermetical closure cap constituted by an annular body 40a and a cylindrical slide portion 40b contiguously rising from the annular body 40a and having an inner diameter slightly larger than the rigid portion 3 of the insert section 2. The annular body 40a is provided with a click mechanism 41 including a click member 41a and a click spring 41b which constantly urges the click member 41a radially inward into engagement with a click groove 42 which is provided on the circumference of the extension 22 of the guide tube 20. The annular body 40a of the hermetical closure cap 40 is further provided with a skirt portion 40c which functions as a partition wall enclosing the hook 30 and preventing its exposure to the outside when the outer sheath 12 is coupled with the guide tube 20 and the insert body 2 of the endoscope as shown in FIG. 5.

Prior to use, the obturator 11 of the trocar 10 is set in the outer sheath 12. On the other hand, the hermetical closure cap 40 is fitted on the hard portion 3 of the insert body 2 of the endoscope, and then the guide tube 20 fitted on the endoscope, joining the extension 22 of the guide tube 20 with the closure cap 40 through the click coupling. In this instance, the slide portion 40b of the closure cap 40 should be engaged with the hard portion 3 in such a manner as to leave substantially no gap space therebetween, but no troubles occur even if the guide tube 20 and the insert portion 2 are spaced from each other by a gap space of a certain width. This means that there may be employed a guide tube 20 with an inside diameter appreciably larger than the outside diameter of the insert portion 2, for the purpose of facilitating the introduction of the insert portion 2, particularly, of the angle portion 4 into the guide tube 20. In addition, the closure cap 40 only needs to be simply fitted on the hard section 3 beforehand.

After insufflation with a pneumoperitoneum gas, the trocar 10 is percutaneously introduced into an intracorporeal cavity, for example, in an abdominal or chest region of a patient's body by piercing the skin in that region with the obturator 11, thereafter advancing the outer sheath to a target point in an intracorporeal cavity which needs observation or remedy. At this time, the outer sheath 12 can be smoothly introduced to an aimed point since the fore end portion of the outer sheath 12 is shaped in the fashion of a sharp-pointed blade and has no stepped portions on its surface. In this state, the obturator 11 is extracted form the outer sheath 12, whereupon the valve 14 is actuated to position the blocking portion 16a across the passage 13 of the outer sheath 12, thereby blocking communication of the intracorporeal cavity with the outside, namely, blocking leaks of the pneumoperitoneum gas through the passage 13.

For inserting the endoscope into the patient's body, the guide tube 20 which receives therein the endoscope in such a manner as to cover the angle portion 4 is placed into the outer sheath 12. Despite the minimal diametral difference between the guide tube 20 and outer sheath 12, the guide tube 20 which is formed of a rigid pipe can be inserted into the latter smoothly and easily. The guide tube 20 thus inserted in the outer sheath 12 is then locked in the coupled state by means of the hook 30 on the outer sheath 12. Consequently, as seen in FIG. 5, the fore end portion 20a of the guide tube 20 is protruded out of the tip end of the outer sheath 12 by a predetermined length l, keeping the insert body 2 out of contact with the tip end 12a of the outer sheath 12. Besides, the hook 30 which is covered under the skirt portion 40c of the hermetical closure cap 40 has no possibility of being inadvertently disengaged from the guide tube 20 during manipulation of the endoscope, preventing the fore end portion 20a of the guide tube 20 from being accidentally retracted into the outer sheath 12.

The angle portion 4 of the insert body 2, which is protruded from the fore end portion 20a of the guide tube 20, can be arcuately turned into a desired direction to observe a particular locality of the intracorporeal cavity or to perform a remedial treatment with the use of forceps, a high frequency knife or other instrument. Such an intracavitary observation or treatment becomes difficult if the cavity is deflated by leakage of the pneumoperitoneum gas to the outside. The guide device of the present invention is free of leaks of the pneumoperitoneum gas since the guide tube 20 is closely fitted in the outer sheath 12 substantially in a hermetically sealed state. The gas leakage through the small gap between the inner periphery of the guide tube 20 and the outer periphery of the insert body 2 is prevented by the slide portion 40b of the closure cap 40 which is fitted on the hard section of the insert body 2 closely in hermetically sealed state. Thus, the intracorporeal cavity is almost completely shielded from the outside.

After an intracavitary examination, diagnosis or remedial treatment, the insert body 2 alone is extracted while fixedly gripping the outer sheath 12 in one hand. At this time, if the angle portion 4 is not in a correctly straightened state, it is contacted with the tip end portion 20a of the guide tube 20 but securely kept out of contact with the tip end 12a of the outer sheath 12. Since the edges of the tip end 20a of the guide tube 20 are arcuately rounded off as described hereinbefore, the insert body 2 can be extracted easily and smoothly, precluding the possibilities of bruises or other damages of the outer skin layer on the angle portion 4 as caused by scratching or scraping action of a sharp edge.

The extraction of the endoscope is met by an increased resisting force as the angle portion 4 comes into abutting engagement with the slide portion 40b of the closure cap 40, and therefore the click mechanism 41 on the closure cap 40 is disengaged from the guide tube 20, permitting to remove the closure cap 40 from the guide tube 20 along with the insert body 2. Consequently, the intracorporeal cavity is communicated with the atmosphere through the guide tube 20 to discharge the pneumoperitoneum gas therethrough without the trouble of operating the valve 14 specifically for this purpose.

Figure 6:
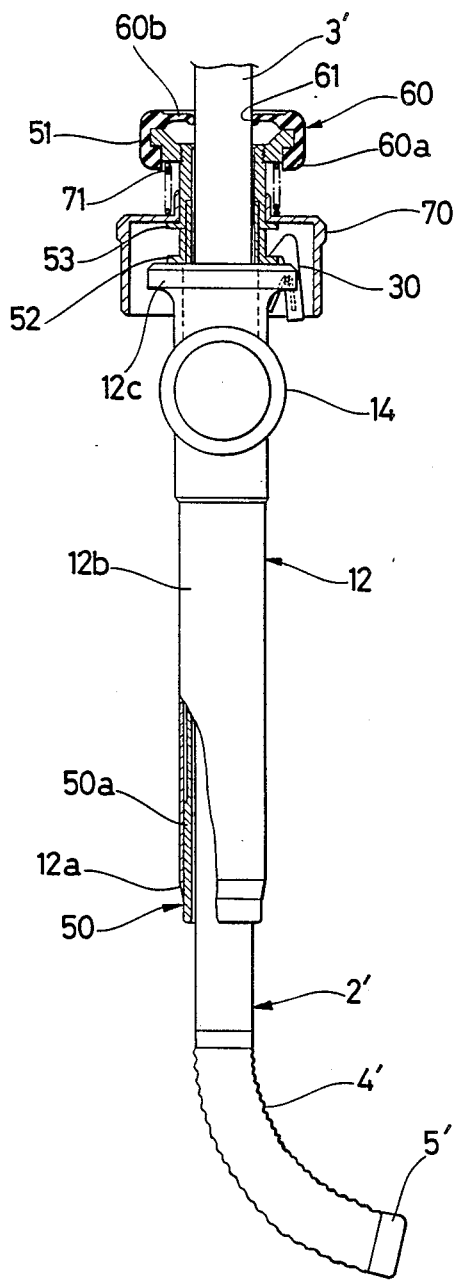
FIG. 6 is a partly cutaway elevation of a second embodiment of the invention, showing major components of the guide tube and endoscope in coupled state.

Illustrated in FIG. 6 is the second embodiment of the invention, employing a guide tube 50 which is adapted to guide an endoscope with an insert body 2' extending forward contiguously from a manipulating portion of the endoscope and having a flexible portion 3' with an outermost soft skin layer of soft material such as rubber, polyurethane or the like, an angle portion 4' and a hart tip end portion 5'.

In case of an endoscope having an insert body 2' with such a flexible portion 3', it is difficult to maintain a hermetical seal by fitting on the flexible portion 3' a closure cap of the construction similar to the cap 40 in the foregoing first embodiment.

Therefore, a seal member 60 of an elastic material like rubber is employed in this embodiment. More specifically, the seal member 60 is provided with a base portion 60a to be detachably fitted around a seal mount member 51 which is contiguously attached to the base end of the guide tube 50, and a seal portion 60b extending radially inward on the upper side of the base portion 60a. For passing the insert body 2' of the endoscope, the seal portion 60b is provided with an aperture 61 of a diameter slightly larger than the outside diameter of the insert body 2'. Upon thrusting the insert body 2' into the aperture 61, the seal portion 60b is abutted against the circumference of the insert body 2' to form a hermetical seal therearound.

The guide tube 50 is provided with a flange 52 in a position close to its base end for interlocking engagement with the hook 30 which is pivotally supported at the base end 12c of the outer sheath 12 for fixing the guide tube 50 in the latter in the coupled state. That is, by engaging the hook 30 with the flange 52, the guide tube 50 and the outer sheath 12 of the trocar 10 are locked in the coupled state. Further, in order to prevent spontaneous disengagement of the hook 30 from the flange 52 during use of the endoscope, a hook cover 70 is fitted on the guide tube 50. This hook cover 70 is slidable between a stopper 53 on the guide tube 50 and the seal mount member 51. Acting on the hook cover member 70 is a spring 71 which urges the cover member 70 into abutting engagement with the stopper 53 to hold the hook 30 in the covered state. Upon pushing the cover member 70 with a finger or fingers to slide upward against the action of the spring 71, the hook member 30 is exposed and can be manipulated into and out of the locking position.

Further, an outwardly bulging thick wall portion 50a is provided at the distal end of the guide tube 50 over a predetermined length. The edge portions at the tip end of the thick wall portion 50 are arcuately rounded off. When the guide tube 50 is placed in the outer sheath 12, the fore end portion 12c of the outer sheath 12 is located on the thick wall portion 50a.

In this case, since the insert body 2' of the endoscope has the flexible portion 3' of a pliable structure rearward of the angle portion 4', it is necessary to provide a gap space of a certain width between the flexible portion 3' and the guide tube 50. However, a hermetical seal is formed between the guide tube 50 and the insert body 2' by the seal portion 60b of the seal member 60 in a secure manner. It follows that there is no possibility of leaks of the pneumoperitoneum gas to the outside, which would cause deflation of the intracorporeal cavity.

Besides, the diametral difference between the guide tube 50 and the outer sheath 12 is minimized at the thick wall portion 50a at the fore end of the guide tube 50, enhancing the air tightness between the guide tube 50 and the outer sheath 12. In this connection, the thick wall portion 50a is relatively short in length and hence its frictional resistance at the time of insertion of the guide tube 50 is small enough to ensure smooth placement of the guide tube into andgout of the outer sheath 12. Further, in a case where the sharp-edged tip end 12a of the outer sheath 12 slightly turned inward, the thick wall portion 60a of the guide tube 50 suffices to have a diametral dimension which ensures its abutting engagement with the inwardly turned tip end. In such a case, the guide tube 50 can be inserted into the outer sheath 12 substantially without any resistance until its fore end comes into abutting engagement with the tip end 12a of the outer sheath 12.

Furthermore, even if the angle portion 4' and flexible portion 3' are in bent state when extracting the insert body 2' of the endoscope, they may be brought into sliding contact with the arcuately rounded-off portions of the guide tube 50 but are kept out of contact with the outer sheath 12 to prevent the bruises or other damages as described hereinbefore.

What is claimed is:

1. A guide device for securing a path of insertion for a percutaneous type endoscope having an insert body with an angle portion closely to the fore end thereof, said guide device comprising:
    a trocar composed of an outer sheath and an obturator extractably inserted in said outer sheath; and
    a guide tube to be inserted into said outer sheath in place of said obturator for forming said path of insertion, said guide tube being so dimensioned as to protrude the fore end thereof from said outer sheath over a predetermined length when placed in said sheath and having at least the inner edge of said fore end rounded off.

2. A guide device as defined in claim 1, wherein said guide tube is formed of a metal pipe.

3. A guide device as defined in claim 1, wherein said guide tube has the fore end thereof rounded off in an arcuate shape in section.

4. A guide device as defined in claim 1, wherein said guide tube is disengageably lockable in said outer sheath.

5. A guide device as defined in claim 1, further comprising a hermetical closure member fitted on part of said insert body and detachably engageable with a base end portion of said guide tube to hold an intracorporeal cavity in hermetically sealed state.

6. A guide device as defined in claim 1, further comprising a seal member of an elastic material fitted on a base end portion of said guide tube in engagement with the circumference of said insert body of said endoscope to provide a hermetical seal between said guide tube and said insert body.

7. A guide device as defined in claim 1, wherein said guide tube is provided with an outwardly bulging thick wall portion on a fore end portion thereof, and the tip end of said outer sheath is located on said thick wall portion when said guide tube is inserted therein.

* * * * *